United States Patent
Locke et al.

(10) Patent No.: US 11,285,256 B2
(45) Date of Patent: Mar. 29, 2022

(54) NEGATIVE PRESSURE WOUND THERAPY SYSTEM

(71) Applicant: KCI LICENSING, INC., San Antonio, TX (US)

(72) Inventors: Christopher B. Locke, Bournemouth (GB); Timothy M. Robinson, Blandford Forum (GB)

(73) Assignee: KCI Licensing, Inc., San Antonio, TX (US)

( * ) Notice: Subject to any disclaimer, the term of this patent is extended or adjusted under 35 U.S.C. 154(b) by 182 days.

(21) Appl. No.: 16/570,715

(22) Filed: Sep. 13, 2019

(65) Prior Publication Data

US 2020/0086014 A1 Mar. 19, 2020

Related U.S. Application Data

(60) Provisional application No. 62/848,380, filed on May 15, 2019, provisional application No. 62/732,220, filed on Sep. 17, 2018.

(51) Int. Cl.
*A61M 1/00* (2006.01)
*A61F 13/00* (2006.01)

(52) U.S. Cl.
CPC ....... *A61M 1/784* (2021.05); *A61F 13/00055* (2013.01); *A61F 13/00068* (2013.01);
(Continued)

(58) Field of Classification Search
CPC .............. A61M 1/0052; A61M 1/0086; A61M 1/0072; A61M 1/0084; A61M 1/0088;
(Continued)

(56) References Cited

U.S. PATENT DOCUMENTS

| 1,355,846 | A | 10/1920 | Rannells |
| 2,547,758 | A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

International Search Report and Written Opinion in International Application No. PCT/US2019/051101, dated Feb. 25, 2020.

(Continued)

*Primary Examiner* — Susan S Su
*Assistant Examiner* — Eric Rassavong

(57) ABSTRACT

A negative pressure wound therapy system includes a dressing, a tube, a flow restriction pad, and an in-line filter. The dressing is configured for placement in a wound bed. The tube includes a first end and a second end. The first end is configured to be operably coupled to the dressing. The second end is configured to engage a negative pressure source. The flow restriction pad is configured to be coupled to the dressing proximate the first end of the tube. The flow restriction pad includes a tortuous fluid flow path that is configured to restrict or reduce an amount of a fluid drawn from the dressing into the tube and induce a backpressure between the dressing and the tube. The in-line filter is positioned within the tube between the first end and the second end. The in-line filter configured to substantially prevent the fluid entering the tube.

7 Claims, 6 Drawing Sheets

(52) U.S. Cl.
CPC ............... *A61M 1/82* (2021.05); *A61M 1/85* (2021.05); *A61M 1/86* (2021.05); *A61M 1/90* (2021.05); *A61M 2205/0238* (2013.01)

(58) Field of Classification Search
CPC ...... A61M 2205/0238; A61F 13/00055; A61F 13/00068; A61F 13/0206
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2009/0000620 A1* | 1/2009 | Virr | A61M 16/142 128/203.27 |
| 2010/0286638 A1 | 11/2010 | Malhi | |
| 2011/0213319 A1* | 9/2011 | Blott | A61M 27/00 604/291 |
| 2014/0343516 A1* | 11/2014 | Coulthard | A61M 1/88 604/319 |
| 2015/0119830 A1* | 4/2015 | Luckemeyer | A61M 1/90 604/319 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |

(56) References Cited

FOREIGN PATENT DOCUMENTS

| WO | 99/13793 A1 | 3/1999 |
|---|---|---|
| WO | WO-2011/135287 A1 | 11/2011 |

OTHER PUBLICATIONS

International Search Report and Written Opinion in International Application No. PCT/US2019/051113, dated Feb. 25, 2020.
Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Phildelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164.
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. KMoscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.

* cited by examiner

NEGATIVE PRESSURE WOUND THERAPY SYSTEM

CROSS-REFERENCE TO RELATED APPLICATIONS

This application claims the benefit of priority to U.S. Provisional Application No. 62/732,220, filed on Sep. 17, 2018, and U.S. Provisional Application No. 62/848,380, filed May 15, 2019, which are each incorporated herein by reference in their entirety.

BACKGROUND

The present disclosure relates generally to wound therapy systems and devices, and more particularly to negative pressure would therapy systems, methods, and devices.

Negative pressure wound therapy (NPWT) is a type of wound therapy that involves applying negative pressure (relative to atmospheric pressure) to a wound site to promote wound healing. Some NPWT systems surround the wound in a dressing which is sealed with a drape. The drape establishes a barrier between negative pressure and atmospheric pressure. The negative pressure is created by a pump which provides suction through a tube to a pad which is coupled to the dressing over the wound site. Due to the suction, fluid from the wound site is drawn into the dressing. The dressing includes a filter that functions to absorb the fluid in an effort to provide only air to the pump. However, sometimes the filter in the dressing eventually becomes saturated with fluid before the dressing is filled. When the filter in the dressing becomes saturated, the NPWT must be interrupted such that the dressing can be replaced. It would be beneficial to provide a dressing that may be substantially filled with fluid, without allowing fluid to travel to the pump.

SUMMARY

One implementation of the present disclosure is a negative pressure wound therapy system includes a dressing, a tube, a flow restriction pad, and an in-line filter. The dressing is configured for placement in a wound bed. The tube includes a first end and a second end. The first end is configured to be operably coupled to the dressing. The second end is configured to engage a negative pressure source. The flow restriction pad is configured to be coupled to the dressing proximate the first end of the tube. The flow restriction pad includes a tortuous fluid flow path that is configured to restrict or reduce an amount of a fluid drawn from the dressing into the tube and induce a backpressure between the dressing and the tube. The in-line filter is positioned within the tube between the first end and the second end. The in-line filter configured to substantially prevent the fluid entering the tube through the flow restriction pad from entering the negative pressure source.

In some embodiments, the dressing is configured to absorb fluid independent of the flow restriction pad or the tube.

In some embodiments, the flow restriction pad further includes a plurality of micro perforations. Each of the plurality of micro perforations is sized to facilitate the passage of air therethrough while inhibiting the passage of fluid therethrough so as to cause the fluid to be absorbed in at least one of the flow restriction pad or the dressing. In some embodiments, the flow restriction pad further includes an adhesive region configured to couple the flow restriction pad to the dressing.

In some embodiments, the dressing does not include a filter and is configured facilitate the passage of fluid and air to the flow restriction pad.

In some embodiments, the tube is configured to absorb fluid and to facilitate evaporation of absorbed fluid. In some embodiments, the negative wound therapy system further includes a fluid trap positioned along the tube and defined by a first diameter. The tube has a second diameter that is substantially less than the first diameter. The fluid trap inhibits the passage of fluid through the tube so as to collect fluid within the fluid trap. In some embodiments, the tube includes an inner surface configured to interface with the fluid. The inner surface includes a coating operable between a first state where the tube has a first aesthetic appearance and a second state where the tube has a second aesthetic appearance different from the first aesthetic appearance. The coating is in the first state when an amount of the fluid in the tube is below a threshold. The coating is in the second state when an amount of the fluid in the tube is at or above the threshold. In some embodiments, the coating is a hydrochromic coating.

In some embodiments, the flow restriction pad further includes a connecting layer including a hydrophobic portion having hydrophobic properties. The flow restriction pad is coupled to the first end of the tube at the hydrophobic portion of the connecting layer. The hydrophobic portion of the connecting layer inhibits the passage of the fluid into the first end of the tube.

Another implementation of the present disclosure is a negative pressure wound therapy system including a dressing, a tube, a flow restriction pad, and an in-line filter. The dressing is configured for placement on a wound bed. The tube includes a first end and a second end. The first end is configured to be operably coupled to the dressing. The second end is configured to engage a negative pressure source. The flow restriction pad is configured to be coupled to the dressing proximate the first end of the tube. The flow restriction pad includes a plurality of micro perforations. Each of the plurality of micro perforations is sized to facilitate the passage of air therethrough while inhibiting the passage of a fluid therethrough so as to cause the fluid to be absorbed in at least one of the flow restriction pad or the dressing. The in-line filter is configured to substantially prevent the fluid entering the tube through the flow restriction pad from entering the negative pressure source and disposed along the tube between the first end of the tube and the second end of the tube.

In some embodiments, the dressing is configured to absorb fluid independent of the flow restriction pad or the tube.

In some embodiments, the flow restriction pad further includes an adhesive region that is configured to couple the flow restriction pad to the dressing.

In some embodiments, the dressing does not include a filter and is configured facilitate the passage of fluid and air to the flow restriction pad.

In some embodiments, the tube is configured to absorb fluid and to facilitate evaporation of absorbed fluid. In some embodiments, the negative pressure wound therapy system further includes a fluid trap that is positioned along the tube and defined by a first diameter. The tube has a second diameter that is substantially less than the first diameter. The fluid trap inhibits the passage of fluid through the tube so as to collect fluid within the fluid trap. In some embodiments, the tube includes an inner surface that is configured to interface with the fluid. The inner surface includes a coating operable between a first state where the tube has a first aesthetic appearance and a second state where the tube has a second aesthetic appearance different from the first aesthetic appearance. The coating is in the first state when an amount of the fluid in the tube is below a threshold. The coating is in the second state when an amount of the fluid in the tube is at or above the threshold. In some embodiments, the coating is a hydrochromic coating.

In some embodiments, the flow restriction pad further includes a connecting layer including a hydrophobic portion having hydrophobic properties. The flow restriction pad is coupled to the first end of the tube at the hydrophobic portion of the connecting layer. The hydrophobic portion of the connecting layer inhibits the passage of the fluid into the first end of the tube. In some embodiments, the flow restriction pad further includes a tortuous fluid flow path configured to restrict or reduce an amount of the fluid drawn from the dressing into the tube and induce a backpressure between the dressing and the tube.

In some embodiments, the tube includes a first section and a second section and the in-line filter includes a first connector, a second connector, and a filter housing. The first section includes the first end and a third end. The second section includes the second end and a fourth end. The first connector is coupled to the third end. The second connector is coupled to the fourth end. The filter housing is coupled to the third end and the fourth end such that the first connector and the second connector are positioned within the filter housing.

Another implementation of the present disclosure is a negative pressure wound therapy system that includes a dressing, a tube, and a flow restriction pad. The dressing is configured for placement in a wound bed. The tube includes a first end and a second end. The first end is configured to be operably coupled to the dressing. The second end is configured to engage a negative pressure source. The flow restriction pad is configured to be coupled to the dressing proximate the first end of the tube. The flow restriction pad includes a plurality of micro perforations and a tortious flow path. Each of the plurality of micro perforations is sized to facilitate the passage of air therethrough while inhibiting the passage of fluid therethrough so as to cause the fluid to be absorbed in at least one of the flow restriction pad or the dressing. The tortuous fluid flow path is configured to restrict or reduce an amount of a fluid drawn from the dressing into the tube and induce a backpressure between the dressing and the tube.

In some embodiments, the dressing is configured to absorb fluid independent of the flow restriction pad or the tube.

In some embodiments, the flow restriction pad further includes an adhesive region configured to couple the flow restriction pad to the dressing.

In some embodiments, the dressing does not include a filter and is configured facilitate the passage of fluid and air to the flow restriction pad.

In some embodiments, the tube is configured to absorb fluid and to facilitate evaporation of absorbed fluid. In some embodiments, the negative pressure wound therapy system further includes a fluid trap positioned along the tube and defined by a first diameter. The tube has a second diameter that is substantially less than the first diameter. The fluid trap inhibits the passage of fluid through the tube so as to collect fluid within the fluid trap.

In some embodiments, the tube includes an inner surface configured to interface with the fluid. The inner surface includes a coating operable between a first state where the tube has a first aesthetic appearance and a second state where the tube has a second aesthetic appearance different from the first aesthetic appearance. The coating is in the first state when an amount of the fluid in the tube is below a threshold. The coating is in the second state when an amount of the fluid in the tube is at or above the threshold. In some embodiments, the coating is a hydrochromic coating.

In some embodiments, the flow restriction pad further includes a connecting layer including a hydrophobic portion having hydrophobic properties. The flow restriction pad is coupled to the first end of the tube at the hydrophobic portion of the connecting layer. The hydrophobic portion of the connecting layer inhibits the passage of the fluid into the first end of the tube. In some embodiments, the negative pressure wound therapy system further includes an in-line filter that is configured to substantially prevent the fluid entering the tube through the flow restriction pad from entering the negative pressure source and disposed along the tube between the first end of the tube and the second end of the tube. In some embodiments, the tube includes a first section and a second section and the in-line filter includes a first connector, a second connector, and a filter housing. The first section includes the first end and a third end. The second section includes the second end and a fourth end. The first connector is coupled to the third end. The second connector is coupled to the fourth end. The filter housing is coupled to the third end and the fourth end such that the first connector and the second connector are positioned within the filter housing.

Another implementation of the present disclosure is a method treating a wound including providing a dressing configured for placement proximate a wound to be treated; providing a flow restriction pad atop the dressing, the flow restriction pad configured to restrict or reduce an amount of fluid drawn from the dressing and through the flow restriction pad; covering the dressing and flow restriction pad with a drape; coupling a tube having a first end and a second end to the drape, with the first end disposed proximate the flow restriction pad; coupling the second end of the tube to a hand-pump, the hand-pump operable to create a negative pressure at the wound; and positioning an in-line filter within the tube between the first end and the second end, the in-line filter configured to substantially prevent the fluid that entered the first end of the tube from entering the hand-pump.

DETAILED DESCRIPTION

Overview

Figure 1:
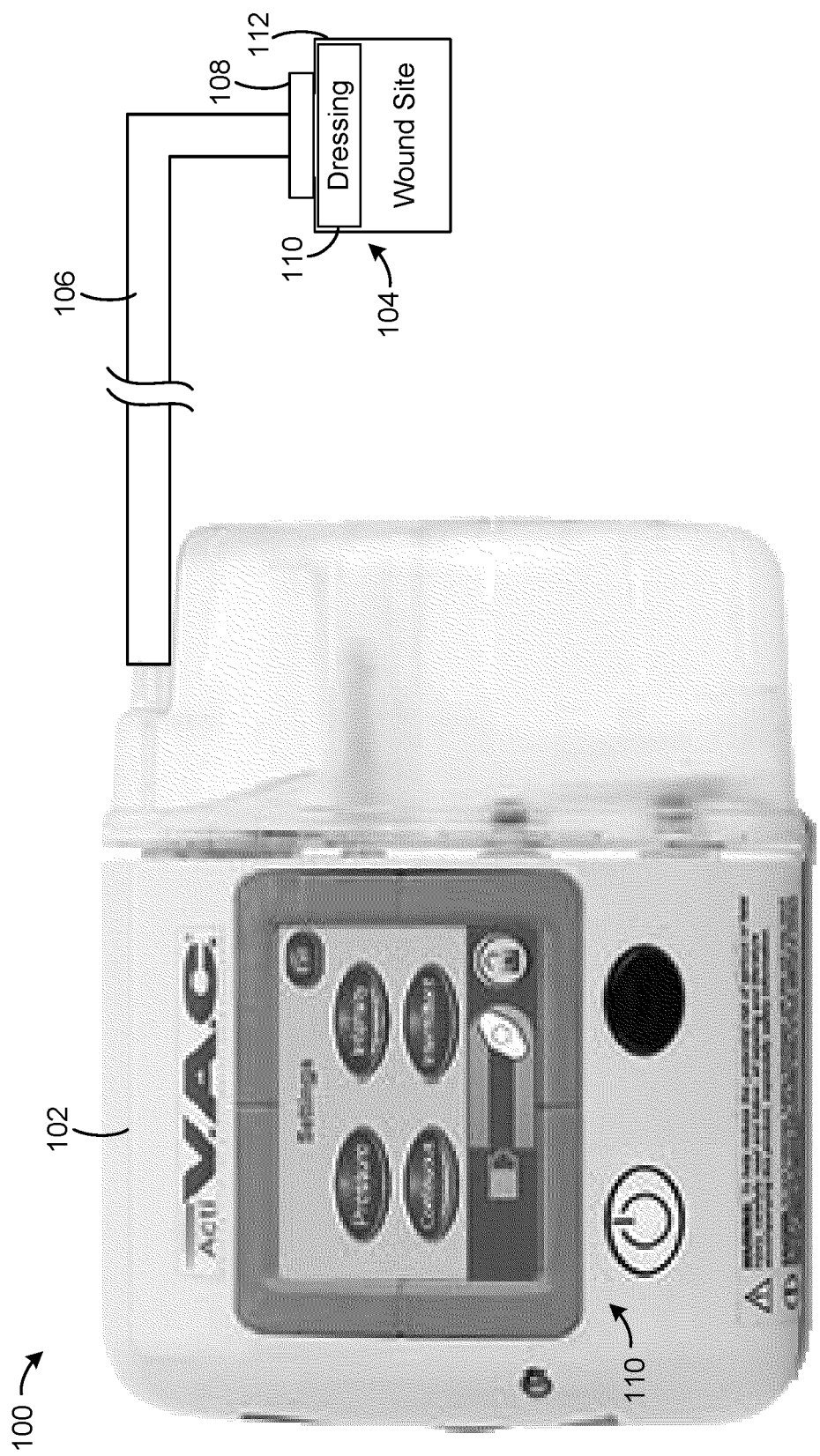
FIG. 1 is a drawing of a negative pressure wound therapy (NPWT) system including a NPWT device fluidly connected with a wound site, according to an exemplary embodiment.

Referring generally to the FIGURES, a negative pressure wound therapy (NPWT) system that includes a tube with an in-line filter and a dressing that does not have a filter, is shown, according to various exemplary embodiments. The dressing is placed on a wound bed (e.g., over a tissue wound, etc.). The NPWT system includes a drape which is placed over the dressing and which seals the dressing and wound bed to create an environment within which negative pressure (e.g., a vacuum, etc.) can be applied. The NPWT system also includes a flow restriction pad which is coupled to the drape and is in fluid communication with the dressing. The tube of the NPWT system is coupled to a negative pressure source and the flow restriction pad.

Once assembled, the NPWT system is operable such that the negative pressure source draws air through the tube to create a vacuum under the drape. The negative pressure draws air and fluid from the wound bed into the dressing. While the dressing does not include a filter, the dressing is configured to absorb the fluid, thereby functioning as a first mechanism for preventing fluid from being provided to the negative pressure source.

The air, and any fluid which is not absorbed by the dressing, is drawn into the flow restriction pad and subsequently into the tube. The flow restriction pad includes a tortious flow path through which the air, and possibly fluid, received from the dressing must traverse prior to encountering micro perforations in the flow restriction pad. The tortious flow path impedes motion of fluid therethrough, while not substantially impeding the flow of air therethrough. In this way, the tortious flow path functions as a second mechanism for preventing fluid from being provided to the negative pressure source.

Air, and any fluid which was not absorbed by the dressing or impeded within the tortious flow path, is provided to the micro perforations. The micro perforations extend through the flow restriction pad and are sized to facilitate the passage of air therethrough while impeding the flow of fluid therethrough. In this way, the micro perforations function as a third mechanism for preventing fluid from being provided to the negative pressure source.

The tube receives air and any fluid which was not absorbed by the dressing, impeded within the tortious flow path, or impeded by the micro perforations. The tube is configured to facilitate evaporation of fluid contained therein. For example, the tube may include portions with an exaggerated surface area which facilitate increased evaporation of the fluid disposed thereon. In this way, the tube functions as a fourth mechanism for preventing fluid from being provided to the negative pressure source.

The tube provides air, and any fluid which was not absorbed by the dressing, impeded within the tortious flow path, impeded by the micro perforations, or evaporated within the tube, to an in-line filter. The in-line filter is configured to collect fluid and facilitate the evaporation of fluid therein. The in-line filter is coupled to a portion of the tube that is further coupled to the negative pressure source. The in-line filter functions to substantially prevent the fluid from being provided to the negative pressure source. In this way, the in-line functions as a fifth mechanism for preventing fluid from being provided to the negative pressure source.

Additionally, various components within the NPWT system may be coated with hydrophobic coatings or constructed from hydrophobic materials so as to impede the transfer of fluid therethrough. In these ways, various components of the NPWT system cooperate to prevent the transmission of fluid to the negative pressure source.

NPWT System

Referring now to FIG. 1, a NPWT system 100 is shown, according to an exemplary embodiment. NPWT system 100 is shown to include a therapy device 102 (e.g., a negative pressure source, a pump, a vacuum pump, etc.) fluidly connected to a wound site 104 via tubing 106 and a manifold 108. Wound site 104 include a tissue wound, a wound dressing 110 that covers the tissue wound and adheres to a patient's skin, and a drape 112 that covers wound dressing 110 and manifold 108. Drape 112 may adhere to wound dressing 110 and/or the patient's skin. Drape 112 facilitates a pressure differential between wound site 104 and a surrounding atmosphere. Wound dressing 110 may be referred to as being a dressing layer and drape 112 may be referred to as a drape layer.

Therapy device 102 can be configured to provide negative pressure wound therapy by reducing the pressure at wound site 104. Therapy device 102 can draw a vacuum at wound site 104 (relative to atmospheric pressure) by removing wound exudate, air, and other fluids from wound site 104 through manifold 108 and tubing 106. Wound exudate may include fluid that filters from a patient's circulatory system into lesions or areas of inflammation. For example, wound exudate may include water and dissolved solutes such as blood, plasma proteins, white blood cells, platelets, and red blood cells. Other fluids removed from wound site 104 may include instillation fluid previously delivered to wound site 104. Instillation fluid can include, for example, a cleansing fluid, a prescribed fluid, a medicated fluid, an antibiotic fluid, or any other type of fluid which can be delivered to wound site 104 during wound treatment. The fluids removed from wound site 104 pass through manifold 108 and then through tubing 106 and may be collected in a canister that is configured to collect wound exudate and other fluids removed from wound site 104. In addition to providing removing exudate, air, and other fluids from wound site 104, tubing 106 may include separate lumens for use by therapy device 102 to measure pressure within wound site 104.

Set Up of a Typical System

When a typical system is set up, a dressing is applied to a wound site and subsequently covered with a drape. The drape is cut to form a hole and a pump is coupled to the drape about the hole. The pump creates suction which draws air and fluid (e.g., wound exudate, blood, tissue, biological material, etc.) found the wound site. The dressing includes a filter that is configured to absorb the fluid, rather than the fluid traveling towards the pump. Apart from the filter, the dressing itself also is configured to absorb fluid. During continued operation of such a typical system, enough fluid may be absorbed in the filter in the dressing that the filter in the dressing becomes saturated. However, the capacity of the filter to absorb fluid is less than the capacity of the dressing to absorb fluid. Due to the saturation of the filter, the dressing must be changed in order to avoid providing fluid to the pump despite additional capacity being present in the dressing. As a result, the NPWT is temporarily interrupted so that the drape can be removed, the dressing changed, and the drape reapplied. During continued NPWT, the dressing may need to be changed multiple times due to the filter in the dressing becoming saturated. Removal of the dressing may be painful to a patient and may impede healing of the wound site. Additionally, each replacement of the dressing increases the cost and length of NPWT which is undesirable to the patient. An opportunity exists to utilize the additional capacity for absorbing fluid provided by the dressing, thereby decreasing the amount of times that the dressing must be changed and therefore making NPWT more desirable.

Even beyond the concerns associated with repetitive changing of the dressing is a concern associated with a difficulty of providing a dressing with a filter which substantially prevents fluid from being provided to the pump. Such a dressing may be complex and expensive to manufacture, and therefore undesirable to the patient.

Example NPWT System with in-Line Filter

Figure 2:
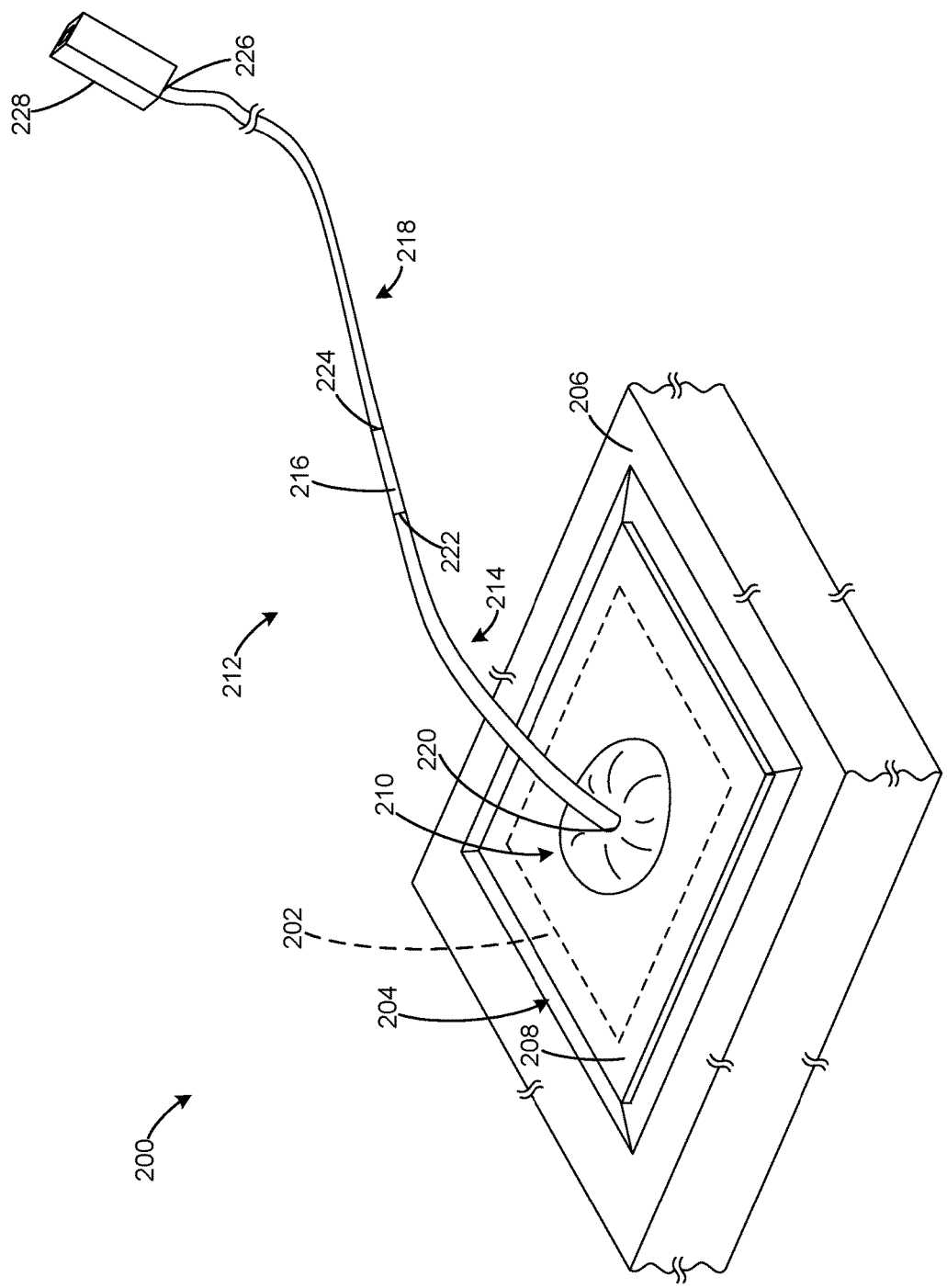
FIG. 2 is a drawing of a NPWT system, according to an exemplary embodiment.

Referring now to FIG. 2, an example NPWT system 200 is shown, according to an exemplary embodiment. NPWT system 200 is utilized in NPWT on a wound bed 202 (e.g., tissue bed, wound site, etc.). When NPWT system 200 is used, air and fluid are drawn from wound bed 202. NPWT system 200 may operate continuously such that an amount of fluid is continuously drawn from wound bed 202. NPWT system 200 is defined by a threshold amount of fluid processing per unit time a. In other words, NPWT system 200 can receive the threshold amount of fluid processing per unit time a over the unit time without being unable to process the fluid received from wound bed 202. As will be explained in more detail herein, NPWT system 200 is configured to have a threshold amount of fluid processing per unit time a that is significantly higher than typical NPWT systems, thereby causing NPWT system 200 to be more desirable than typical NPWT systems.

NPWT system 200 includes a dressing 204 configured to be applied over wound bed 202. Unlike other dressings utilized in typical NPWT systems, dressing 204 does not include a filter (e.g., dressing 204 is configured to facilitate the transfer of air and fluid therethrough, etc.). As a result, NPWT system 200 is not dependent on a filter in dressing 204 for preventing the transfer of fluid to a negative pressure source, such as therapy device 102, of NPWT system 200. Additionally, dressing 204 may be considerably less expensive than dressings which include a filter, therefore making NPWT system 200 more desirable than typical NPWT systems.

Dressing 204 is configured to absorb (e.g., soak up, retain, etc.) fluid from wound bed 202 at an absorption rate $r_{Dressing}$ of dressing 204 until dressing 204 becomes saturated (e.g., satiated, etc.). Dressing 204 becomes saturated when an amount of fluid absorbed within dressing 204 reaches a threshold (e.g., z milliliters, etc.) $V_{Dressing}$. The threshold amount of fluid processing per unit time a of NPWT system 200 is related to the threshold $V_{Dressing}$ of dressing 204 and the absorption rate of dressing 204. For example, the greater the absorption rate $r_{Dressing}$ of dressing 204 and/or the threshold $V_{Dressing}$ of dressing 204, the greater the threshold amount of fluid processing per unit time a of NPWT system 200.

The threshold $V_{Dressing}$ of dressing 204 and/or the absorption rate $r_{Dressing}$ of dressing 204 may be defined by a material of dressing 204, dimensions (e.g., thickness, length, width, etc.) of dressing 204, a weave structure of dressing 204, and other similar parameters. In various embodiments, dressing 204 is made from polyurethane (e.g., thermoplastic polyurethane, Tecophilic™ HP-93A-100 from the Lubrizol Corporation, etc.). In some embodiments, dressing 204 contains an absorbent (e.g., superabsorbent, etc.) material contained (e.g., integrated, incorporated, etc.) therein. For example, dressing 204 may be woven with various fibers made from superabsorbent material. While not including a filter, the absorbent properties of dressing 204 mitigate the transfer of fluid through dressing 204 and thereby assist in protecting a negative pressure source of NPWT system 200 from fluid.

NPWT system 200 includes a drape 206. Drape 206 is configured to be placed on and cover a top surface 208 of dressing 204. NPWT system 200 also includes a flow restriction pad 210. Flow restriction pad 210 is configured to be placed on top surface 208 of dressing 204. Flow restriction pad 210 is placed within a hole (e.g., aperture, etc.) in drape 206. Flow restriction pad 210 is configured to receive air and fluid from dressing 204 and to provide the air and fluid through drape 206. Flow restriction pad 210 may seal to drape 206 such that the transfer of air and fluid between flow restriction pad 210 and drape 206 is substantially prevented. As will be explained in more detail herein, flow restriction pad 210 may be configured to slow the transfer of fluid through dressing 204, thereby causing the fluid to be exposed to dressing 204 for a longer period of time resulting in additional fluid being absorbed within dressing 204. Accordingly, the configuration of flow restriction pad 210 is also a factor in determining the threshold amount of fluid processing per unit time a of NPWT system 200.

In various embodiments, flow restriction pad 210 is made from a material that facilitates rapid evaporation such as polyurethane (e.g., thermoplastic polyurethane, Tecophilic™ HP-93A-100 from the Lubrizol Corporation, etc.). In some embodiments, flow restriction pad 210 is coated with a hydrophobic material to mitigate ingress of fluid into the tube 212.

NPWT system 200 also includes a tube 212 (e.g., tube set, conduit, etc.). Tube 212 is configured to be coupled to a negative pressure source of NPWT system 200 and to flow restriction pad 210. Tube 212 is configured to transfer suction (e.g., a vacuum, etc.) produced by the negative pressure source to wound bed 202 such that fluid and air are drawn from wound bed 202. In various embodiments, tube 212 is transparent (e.g., clear, etc.) and/or translucent so as to facilitate evaporation of fluid contained therein.

In various embodiments, tube 212 is configured to absorb fluid at an absorption rate $r_{Tube}$ and/or facilitate rapid evaporation of fluid contained therein at an evaporation rate $e_{Tube}$, thereby increasing the threshold amount of fluid processing per unit time a of NPWT system 200. For example, tube 212 may absorb fluid until tube 212 becomes saturated. Tube 212 may become saturated when an amount of fluid absorbed within tube 212 reaches a threshold (e.g., w milliliters, etc.) $V_{Tube}$. The threshold amount of fluid processing per unit time a of NPWT system 200 is related to the threshold $V_{Tube}$ of tube 212, the absorption rate $r_{Tube}$ of tube 212, and/or the evaporation rate $e_{Tube}$ of tube 212. For example, the greater the absorption rate $r_{Tube}$ of tube 212, the threshold $V_{Tube}$ of tube 212, and/or the evaporation rate $e_{Tube}$ of tube 212, the greater the threshold amount of fluid processing per unit time a of NPWT system 200.

The threshold $V_{Tube}$ of tube 212, the absorption rate $r_{Tube}$ of tube 212, and/or the evaporation rate $e_{Tube}$ of tube 212 may be defined by a material of tube 212, dimensions (e.g., thickness, length, width, etc.) of tube 212, a weave structure of tube 212, and other similar parameters. In this way, both tube 212 and dressing 204 may absorb fluid. For example, tube 212 may be made from a material that facilitates rapid evaporation such as polyurethane (e.g., thermoplastic polyurethane, Tecophilic™ HP-93A-100 from the Lubrizol Corporation, etc.). By absorbing fluid and/or facilitating evaporation of fluid, tube 212 supplements the absorbing ability of dressing 204 to provide a relatively high threshold amount of fluid processing per unit time a for NPWT system 200 compared to typical NPWT systems which utilize a dressing having a filter. In various embodiments, tube 212 has a thickness of between 0.4 millimeters (mm) and 1.5 mm, inclusive, and an inner diameter of between 1.9 mm and 4 mm, inclusive. In some embodiments, tube 212 is configured to have an exaggerated inner surface area (e.g., using internal features, etc.) to facilitate increased absorption and evaporation of fluid disposed thereon.

In operation, the air is drawn through dressing 204, under drape 206, through flow restriction pad 210, through a first section 214 of tube 212, through an in-line filter 216 (e.g., air-fluid separator, filter cartridge, etc.), and through a second section 218 of tube 212 to the negative pressure source. In-line filter 216 is configured to separate the fluid and air received from first section 214 of tube 212 such that the fluid remains in in-line filter 216 while the air is provided to second section 218 of tube 212. In this way, in-line filter 216 substantially prevents fluid from being provided to the negative pressure source.

In-line filter 216 is configured to contain a threshold amount of fluid therein (e.g., v milliliters, etc.) $V_{Filter}$. In-line filter 216 may also facilitate evaporation of fluid contained therein at an evaporation rate $e_{Filter}$. In these ways, in-line filter 216 functions to substantially increase the threshold amount of fluid processing per unit time a of NPWT system 200. For example, in-line filter 216 may collect fluid until an amount of fluid within in-line filter 216 is equal to the threshold amount $V_{Filter}$ of fluid. The threshold amount of fluid processing per unit time a of NPWT system 200 is related to the threshold amount of in-line filter 216. For example, the greater the threshold amount $V_{Filter}$ of in-line filter 216, the greater the threshold amount of fluid processing per unit time a of NPWT system 200.

The threshold amount $V_{Filter}$ and evaporation rate $e_{Filter}$ of in-line filter 216 may be defined by a material of tube 212, dimensions (e.g., thickness, length, width, etc.) of tube 212, a weave structure of tube 212, and other similar parameters. In this way, both tube 212 and dressing 204 may absorb fluid. For example, tube 212 may be made from a material that facilitates rapid evaporation such as polyurethane (e.g., thermoplastic polyurethane, Tecophilic™ HP-93A-100 from the Lubrizol Corporation, etc.). By absorbing fluid and/or facilitating evaporation of fluid, tube 212 supplements the absorbing ability of dressing 204 to provide a relatively high threshold amount of fluid processing per unit time a for NPWT system 200 compared to typical NPWT systems which utilize a dressing having a filter.

In some embodiments, in-line filter 216 is a non-gelling cylindrical filter. For example, in-line filter 216 may be a sintered polymer filter (e.g., a Porex sintered polymer filter, a Porvair sintered polymer filter, etc.). In other embodiments, in-line filter 216 is a cartridge filter. For example, in-line filter 216 may include a thin membrane. This membrane may be made from, for example, Gore® MMT-314. In these embodiments, tube 212 may be constructed from a relatively absorbent and evaporative material, such as polyurethane (e.g., thermoplastic polyurethane, Tecophilic™ HP-93A-100 from the Lubrizol Corporation, etc.) or a highly absorbent polymer (e.g., Tecophilic™ TG2000, etc.). In other embodiments, in-line filter 216 may include a carboxymethyl cellulose (CMC) absorbent. For example, the in-line filter 216 may include a CMC absorbent dispersed in a polymer, such as a polymer with a relatively high moisture vapor transmission rate (MVTR). In this example, the CMC absorbent and the polymer may be coextruded. The CMC absorbent may also be coated from a solvent (e.g., organic solvent, etc.) solution.

First section 214 includes a first end 220 and a second end 222. First end 220 is configured to be coupled (e.g., operatively coupled, etc.) to flow restriction pad 210 and second end 222 is configured to be coupled to in-line filter 216. For example, first end 220 may be received within or may receive a fitting of flow restriction pad 210. Similarly, second end 222 may be received within or may receive a fitting of in-line filter 216.

Second section 218 includes a third end 224 and a fourth end 226. Third end 224 is configured to be coupled to in-line filter 216 and fourth end 226 is configured to be coupled to a connector 228. For example, third end 224 may be received within or may receive a fitting of in-line filter 216. Similarly, fourth end 226 may be received within or may receive a fitting of connector 228. Connector 228 is configured to be received within a corresponding connector on the negative pressure source of NPWT system 200 such that fourth end 226 is engaged with the negative pressure source.

In some embodiments, tube 212 is continuous and does not include first end 220 and second end 222. Instead, in-line filter 216 is positioned within tube 212. In these embodiments, in-line filter 216 may have an outer diameter slightly larger than an inner diameter of tube 212, such that in-line filter 216 may be inserted into tube 212 and tube 212 may seal around in-line filter 216.

A user is alerted that dressing 204 has become saturated when fluid is visible within tube 212. At this time, the user may temporarily stop NPWT and change dressing 204 and/or drain fluid from tube 212 and/or in-line filter 216.

In various embodiments, NPWT system 200 includes additional filters, similar to in-line filter 216, downstream of in-line filter 216. In this way, NPWT system 200 can continue to operate in the event of a failure of in-line filter 216 without providing fluid to the negative pressure source.

Example Flow Restriction Pad

Figure 3:
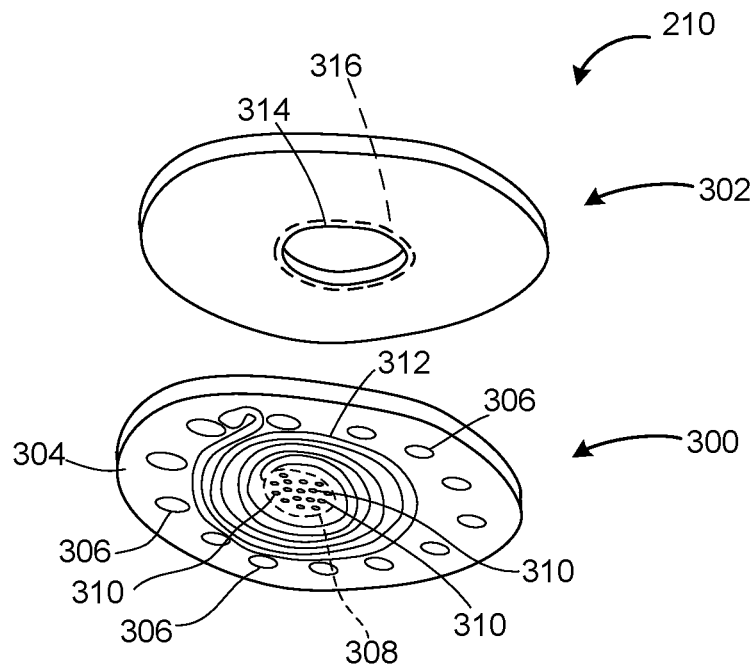
FIG. 3 is a top exploded view of a flow restriction pad for use in a NPWT system, such as the NPWT system shown in FIG. 2, according to an exemplary embodiment.
Figure 4:
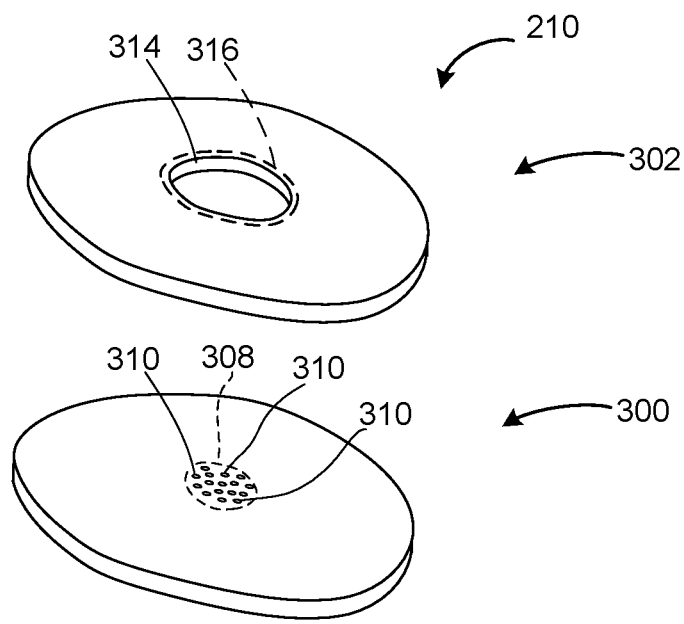
FIG. 4 is a bottom exploded view of a flow restriction pad for use in a NPWT system, such as the NPWT system shown in FIG. 2, according to an exemplary embodiment.

Referring now to FIGS. 3 and 4, flow restriction pad 210 is shown and described in greater detail. Flow restriction pad 210 includes a interfacing portion 300 (e.g., interfacing portion, etc.) and an connecting portion 302 (e.g., connecting portion, etc.). Interfacing portion 300 is configured to interface with dressing 204 and connecting portion 302 is configured to interface with tube 212 and drape 206. In various embodiments, interfacing portion 300 and connecting portion 302 are structurally integrated and are inseparable. In other embodiments, interfacing portion 300 and connecting portion 302 are manufactured separately and are subsequently inseparably coupled together (e.g., using adhesive, etc.). For example, interfacing portion 300 may be molded (e.g., injection molded, etc.) and connecting portion 302 may be woven. In such an example, interfacing portion 300 may be adhesively bonded to connecting portion 302 to form flow restriction pad 210. While flow restriction pad 210 is shown as being cylindrical, it is understood that flow restriction pad 210 may be rectangular, prismatic, hexagonal, polygonal, and otherwise similarly shaped.

Interfacing portion 300 includes a lower surface 304. Lower surface 304 is configured to interface with dressing 204. Interfacing portion 300 also includes a plurality of retention members 306 (e.g., adhesive regions, locating members, engagement members, etc.) disposed on (e.g., positioned on, disposed along, etc.) lower surface 304. Each retention member 306 is configured to engage with dressing 204 to resist movement of interfacing portion 300, and therefore of flow restriction pad 210, relative to dressing 204. In various embodiments, retention members 306 are adhesive regions. In other embodiments, retention members 306 are hook and loop fasteners (e.g., Velcro®, etc.).

In various embodiments, retention members 306 are disposed proximate a perimeter of lower surface 304. In other embodiments, retention members 306 may be disposed in patterns along lower surface 304, such as in the shape of a cross or in a plurality of concentric rows. While retention members 306 are shown as circular, it is understood that retention members 306 may be square, rectangular, hexagonal, triangular, polygonal, or otherwise similarly shaped. In some embodiments, interfacing portion 300 does not include retention members 306. In these embodiments, flow restriction pad 210 may be retained relative to dressing 204 via drape 206.

Interfacing portion 300 also includes a perforated region 308 disposed on lower surface 304. In an exemplary embodiment, perforated region 308 is centered on lower surface 304 (e.g., perforated region 308 has a centroid that is coincident with a center axis of interfacing portion 300, perforated region 308 has a centroid that is coincident with a centroid of lower surface 304, etc.). However, perforated region 308 may be otherwise positioned. For example, interfacing portion 300 may include a plurality of perforated regions 308, each of the plurality of perforated regions 308 symmetrically disposed along lower surface 304. In some embodiments, perforated region 308 is generally circular. However, in other embodiments perforated region 308 may be square, rectangular, ellipsoidal, triangular, hexagonal, or otherwise similarly shaped.

Interfacing portion 300 includes a plurality of micro perforations 310 (e.g., micro-perforations, apertures, holes, etc.) located within perforated region 308. Micro perforations 310 each facilitate communication through interfacing portion 300 by air but mitigation communication through interfacing portion 300 by fluid, thereby enabling absorption of the fluid within dressing 204 or within flow restriction pad 210. Specifically, micro perforations 310 are configured to transfer suction from tube 212 to dressing 204 while mitigating the transfer of fluid from wound bed 202 to tube 212. Micro perforations 310 may be sized or otherwise configured to inhibit the transfer of fluid therethrough (e.g., a diameter of each of micro perforations 310 is less than a diameter of a target fluid droplet, etc.).

In an exemplary embodiment, perforated region 308 is centered on lower surface 304, thereby causing micro perforations 310 to be centered on lower surface 304. In such an embodiment, suction from the negative pressure source may be directed across lower surface 304 substantially evenly, thereby mitigating fluid accumulation at various locations on dressing 204. In some embodiments, interfacing portion 300 includes between fifty and one-hundred micro perforations 310, inclusive.

Micro perforations 310 are formed by an implement (e.g., laser, needle, pin, hot wire, radio-frequency device, ultrasonic device, etc.). Micro perforations 310 are defined by a cross-sectional shape. In various embodiments, the cross-sectional shape of micro perforations 310 is circular. However, in other embodiments, the cross-sectional shape of micro perforations 310 may be square, rectangular, triangular, polygonal, hexagonal, or otherwise similarly shaped. In some embodiments, some of micro perforations 310 have one cross-sectional shape (e.g., circular, etc.) while others of micro perforations 310 have another cross-sectional shape (e.g., ellipsoidal, etc.). Furthermore, micro perforations 310 are substantially uniformly disposed within perforate region 308. Therefore, by using perforated regions 308 of different shapes, sizes, and configurations, interfacing portion 300 may include more or less micro perforations 310.

In various embodiments, micro perforations 310 are coated with a hydrophobic coating. The hydrophobic coating functions to inhibit the transfer of fluid through micro perforations 310 while facilitating the transfer of air through micro perforations 310. In additional to such a hydrophobic coating, retention members 306 may be hydrophobic and function to mitigate transfer of fluid through interfacing portion 300. For example, retention member 306 may be a series of concentric (e.g., sharing the same center point, etc.) circles configured to form circular hydrophobic seals along dressing 204.

Interfacing portion 300 also includes a tortious flow pathway 312 (e.g., circuitous pathway, winding pathway, etc.) extending along or within lower surface 304. Tortious flow pathway 312 is configured to restrict or reduce an amount of fluid drawn through flow restriction pad 210 from dressing 204. In this way, tortious flow pathway 312 is configured to induce a backpressure between dressing 204 and tube 212.

Tortious flow pathway 312 may be defined by adjacent ribs (e.g., walls, etc.) protruding from lower surface 304 and forming a channel therebetween or may be defined by a channel within lower surface 304 itself. Air can be directed from various locations on dressing 204 to micro perforations 310 via tortious flow pathway 312. Tortious flow pathway 312 is configured to further mitigate the transfer of fluid through interfacing portion 300. Due to the tortious nature of tortious flow pathway 312, fluid is impeded from traversing tortious flow pathway 312 to micro perforations 310. In some embodiments, tortious flow pathway 312 is spiral shaped. However, in other embodiments, tortious flow pathway 312 may be zig-zag shaped or otherwise shaped to provide tortious flow path for fluid and air to travel from dressing 204 to micro perforations 310. Lower surface 304 may also include a plurality of tortious flow pathways 312.

Connecting portion 302 includes a connecting aperture 314 and a hydrophobic portion 316 surrounding connecting aperture 314. Connecting aperture 314 is configured to be coupled to tube 212. While not shown, connecting aperture 314 may include a fitting configured to receive or be received within tube 212. Connecting aperture 314 is centered over perforated region 308. In various embodiments, perforated region 308 is circular, connecting aperture 314 is circular, and connecting aperture 314 has substantially the same diameter as perforated region 308. Hydrophobic portion 316 is hydrophobic (e.g., is coated with a hydrophobic coating, etc.) and is configured to impede fluid flow into tube 212 when tube 212 is coupled to connecting portion 302.

Example in-Line Fluid Trap

Figure 5:
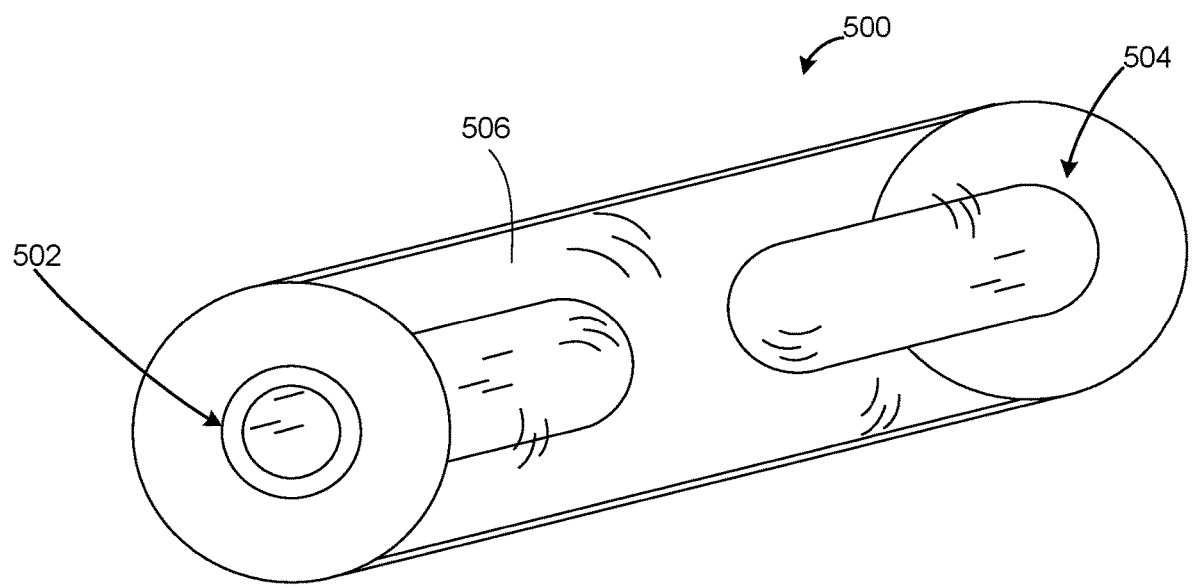
FIG. 5 is a drawing of an in-line filter for use in a NPWT system, such as the NPWT system shown in FIG. 2, according to an exemplary embodiment.

Referring now to FIG. 5, an in-line fluid trap 500 is shown, according to an exemplary embodiment. In-line fluid trap 500 is configured to be implemented in NPWT system 200 in place of, or in addition to, in-line filter 216. For example, in-line fluid trap 500 may be coupled to first section 214 and to second section 218. In-line fluid trap 500 is configured to collect fluid provided from flow restriction pad 210 through tube 212 and to facilitate evaporation of collected fluid within in-line fluid trap 500 so as to impede the transfer of fluid to the negative pressure source.

In-line fluid trap 500 includes a first connector 502 and a second connector 504. First connector 502 and second connector 504 are configured to be coupled to tube 212. For example, first connector 502 may receive second end 222 of tube 212 therein and second connector 504 may also receive third end 224 of tube 212 therein. First connector 502 and second connector 504 may include porous components configured to permit the flow of air therethrough but to impede the flow of fluid therethrough.

In-line fluid trap 500 includes a filter housing 506. Filter housing 506 is coupled to first connector 502 and second connector 504 such that first connector 502 and second connector 504 are each positioned within filter housing 506. Filter housing 506 has a diameter that is larger than a diameter of tube 212. For example, filter housing 506 may have a diameter that is 150% of a diameter of tube 212. Through filter housing 506, in-line fluid trap 500 may provide tube 212 with an area of increased surface area from which fluid can be evaporated. Similar to tube 212, filter housing 506 may be transparent (e.g., clear, etc.) and/or translucent so as to facilitate evaporation of fluid contained therein.

In some embodiments, in-line fluid trap 500 includes absorbent positioned therein. For example, in-line fluid trap 500 may contain absorbent particles configured to absorb fluid within in-line fluid trap 500. Such absorbent may provide an additional mechanism for mitigating the transfer of fluid to the negative pressure source of NPWT system 200. Such absorbents may be, for example, non-woven absorbents (e.g., TAL2 manufactured by Technical Absorbents, etc.).

Example Tube

Figure 6:
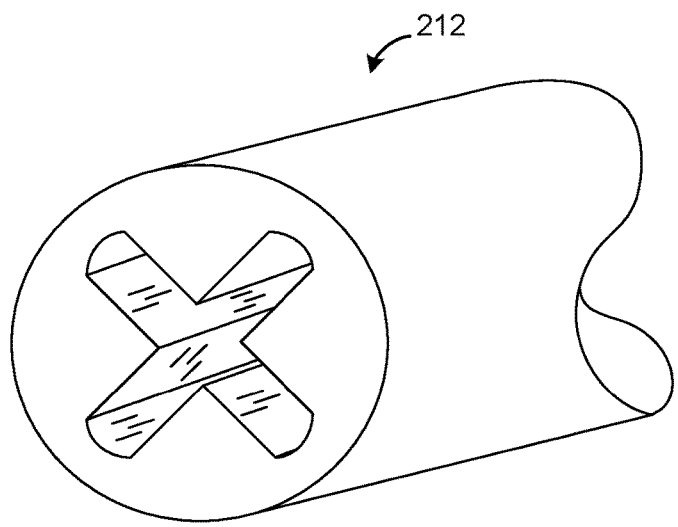
FIG. 6 is a cross-sectional view of a tube for use in a NPWT system, such as the NPWT system shown in FIG. 2, according to an exemplary embodiment.
Figure 7:
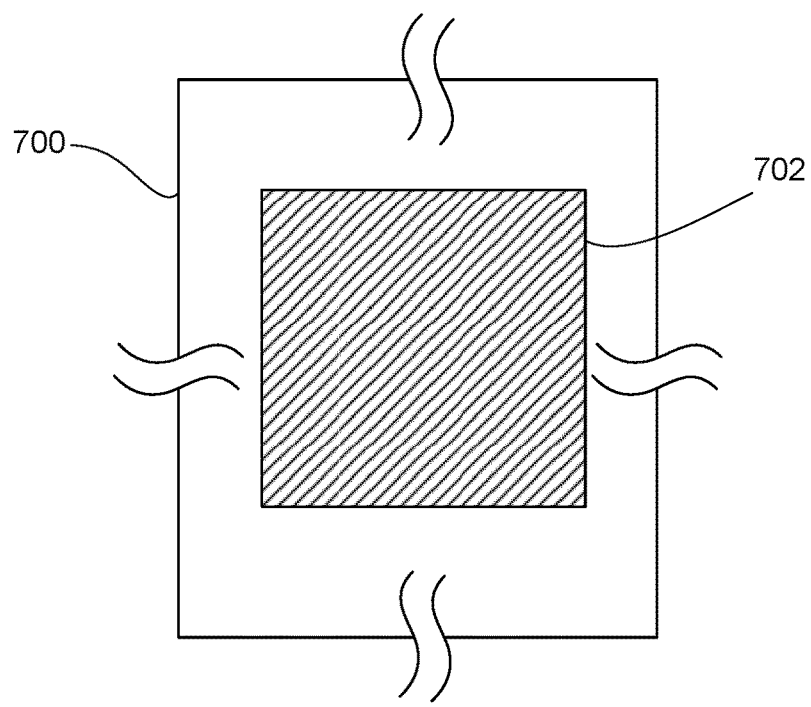
FIG. 7 is a top view of an inner surface of a tube for use in a NPWT system, such as the NPWT system shown in FIG. 2, in a first state, according to an exemplary embodiment.
Figure 8:
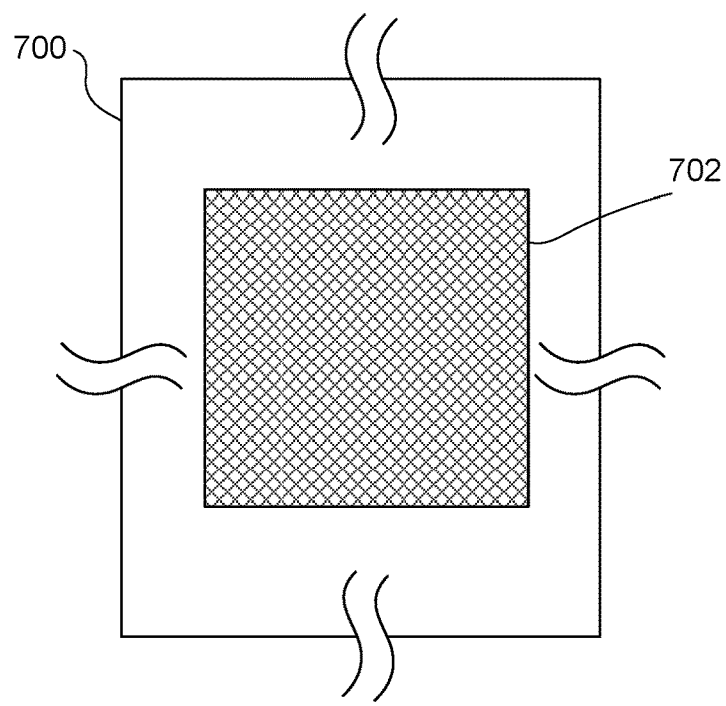
FIG. 8 is a top view of an inner surface of a tube for use in a NPWT system, such as the NPWT system shown in FIG. 2, in a second state, according to an exemplary embodiment.

Referring now to FIGS. 6-8, tube 212 is shown, according to an exemplary embodiment. In this embodiment, tube 212 does not have a circular inner surface. Instead, tube 212 utilizes a shaped inner conduit within which fluid is provided. Such a shaped inner conduit may provide the fluid with additional surface area with which to adhere such that additional fluid can be evaporated from within tube 212.

FIGS. 7 and 8 illustrate a top view of tube 212 showing an inner surface 700 of tube 212. Tube 212 includes a fluid indicator 702 disposed on inner surface 700 of tube 212. Inner surface 700 is operable between a first state, where an amount of fluid within tube 212 is below a threshold, and a second state, where an amount of fluid within tube 212 is above a threshold. Fluid indicator 702 is configured to change aesthetic appearances based upon the state of inner surface 700. For example, when the amount of fluid within tube 212 is below the threshold, inner surface 700 is in the first state and fluid indicator 702 has a first aesthetic appearance, as shown in FIG. 7. However, when the amount of fluid within tube 212 is above a threshold, inner surface 700 is in the second state and fluid indicator 702 has a second aesthetic appearance, as shown in FIG. 8. Using fluid indicator 702, a user can quickly determine if NPWT should be stopped and dressing 204 replaced.

In various embodiments, fluid indicator 702 may include a hydrochromatic coating (e.g., coatings manufactured by SFXC®, coating manufactured by LCRHallcrest, etc.) configured to become transparent based upon an amount of fluid within tube 212. In such embodiments, fluid indicator 702 may include a written message (e.g., text, image, graphic, etc.) or color which is hidden by the hydrochromatic coating when the amount of fluid within tube 212 is below the threshold but is revealed once the amount of fluid within tube 212 is above the threshold. Such a hydrochromatic coating may be reversible such that when fluid is removed from tube 212 (e.g., by evaporation, by draining, etc.), the message or color is hidden. In other embodiments, fluid indicator 702 is irreversible and indicates that tube 212 contains or has contained an amount of fluid above the threshold.

Kit for Use with a NPWT System

Figure 9:
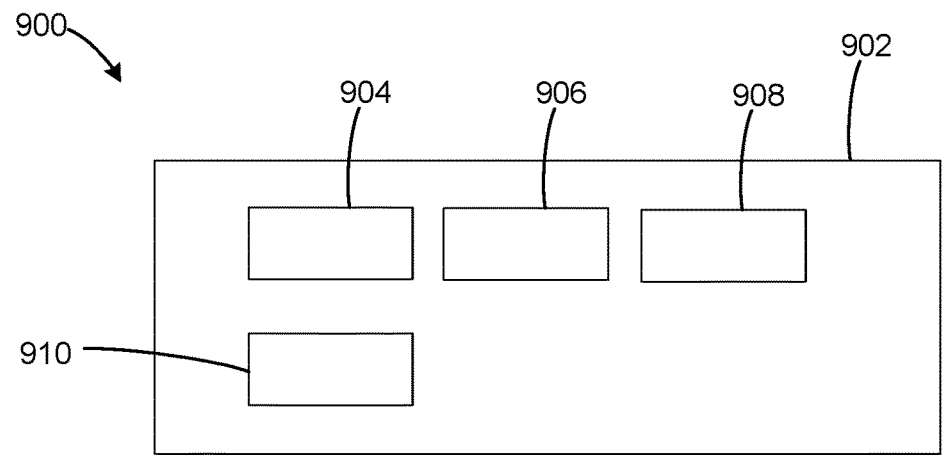
FIG. 9 is a block diagram of a kit for use with an NPWT system, according to an exemplary embodiment.

Referring now to FIG. 9, a kit 900 is shown, according to an exemplary embodiment. Kit 900 is for use with a NPWT system, such as NPWT system 200. Kit 900 includes a package 902. Package 902 defines a sterilized interior environment. Package 902 may be a bag, a case, and other similar structures. Kit 900 also includes a dressing layer 904. Dressing layer 904 is disposed within package 902. Dressing layer 904 may be dressing 204. Kit 900 also includes a drape layer 906. Drape layer 906 is disposed within package 902. Drape layer 906 may be drape 206. Kit 900 also includes a flow restriction pad 908. Flow restriction pad 908 is disposed within package 902. Flow restriction pad 908 may be flow restriction pad 210. Kit 900 also includes a tube 910. Tube 910 is disposed within package 902. Tube 910 may be tube 212.

Method of Cutting a Drape for Use with a NPWT Device

Figure 10:
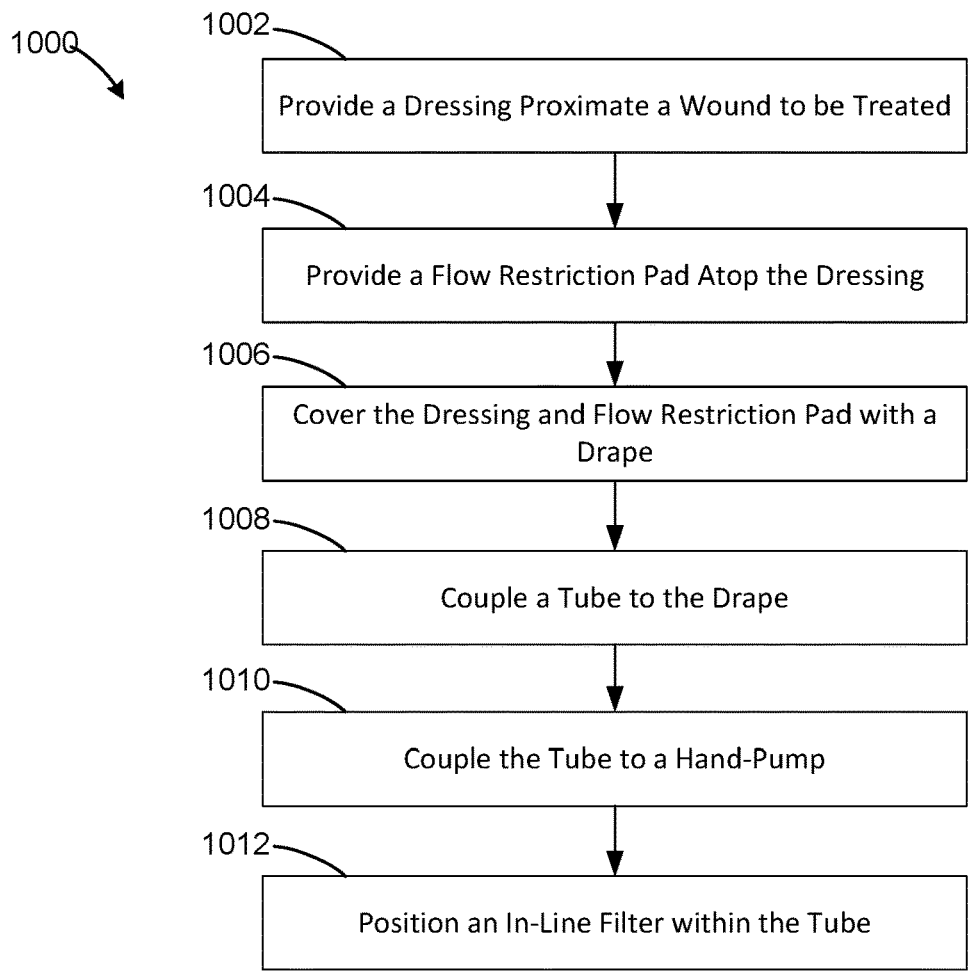
FIG. 10 is a block diagram of a method of treating a wound using an NPWT system, according to an exemplary embodiment.

Referring now to FIG. 10, a method 1000 of treating a wound is shown, according to an exemplary embodiment. Method 1000 is implemented with a NPWT system, such as NPWT system 200. Method 1000 includes, in block 1002, providing a dressing, such as dressing 204, that is configured for placement proximate a wound to be treated. Method 1000 also includes, in block 1004, providing a flow restriction pad, such as flow restriction pad 210, atop the dressing. Like flow restriction pad 210, the flow restriction pad is configured to restrict or reduce an amount of fluid drawn from the dressing and through the flow restriction pad. Method 1000 also includes, in block 1006, covering the dressing and flow restriction pad with a drape, such as drape 206. Method 1000 also includes, in block 1008, coupling a tube, such as tube 212, to the drape. Specifically, the tube includes a first end and a second end, and the tube is coupled to the drape, in block 1008, such that the first end of the tube is disposed proximate the flow restriction pad. Method 1000 also includes, in block 1010, coupling the tube to a hand-pump. Specifically, the tube is coupled to the hand-pump, in block 1010, such that the second end of the tube is coupled to the hand-pump. The hand-pump may operate as the negative pressure source previously described. Method 1000 also includes, in block 1012, positioning an in-line filter, such as in-line filter 216, within the tube. Specifically, the in-line filter is positioned within the tube, in block 1012, between the first end of the tube and the second end of the tube. The in-line filter is configured to substantially prevent the fluid that entered the first end of the tube from entering the hand pump (e.g., via the second end of the tube, etc.).

CONFIGURATION OF EXEMPLARY EMBODIMENTS

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure can be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps can be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A negative pressure wound therapy system comprising:
    a dressing configured for placement in a wound bed;
    a tube configured to absorb fluid and to facilitate evaporation of the absorbed fluid, the tube comprising:
        a first end configured to be operably coupled to the dressing;
        a second end configured to engage a negative pressure source; and
        an inner surface configured to interface with the fluid, the inner surface comprising a coating operable between a first state where the tube has a first aesthetic appearance and a second state where the tube has a second aesthetic appearance different from the first aesthetic appearance;
    a flow restriction pad configured to be coupled to the dressing proximate the first end of the tube, the flow restriction pad comprising a tortuous fluid flow path configured to restrict or reduce an amount of a fluid drawn from the dressing into the tube and induce a backpressure between the dressing and the tube; and
    an in-line filter positioned within the tube between the first end and the second end, the in-line filter configured to substantially prevent the fluid entering the tube through the flow restriction pad from entering the negative pressure source.

2. The negative pressure wound therapy system of claim 1, wherein the dressing is configured to absorb fluid independent of the flow restriction pad or the tube.

3. The negative pressure wound therapy system of claim 1, wherein the flow restriction pad further comprises a plurality of micro perforations, each of the plurality of micro perforations sized to facilitate the passage of air therethrough while inhibiting the passage of fluid therethrough so as to cause the fluid to be absorbed in at least one of the flow restriction pad or the dressing.

4. The negative pressure wound therapy system of claim 1, wherein the dressing does not comprise a filter and is configured to facilitate the passage of fluid and air to the flow restriction pad.

5. The negative pressure wound therapy system of claim 1, further comprising a fluid trap positioned along the tube and defined by a first diameter;
    wherein the tube has a second diameter that is substantially less than the first diameter; and
    wherein the fluid trap inhibits the passage of fluid through the tube so as to collect fluid within the fluid trap.

6. The negative pressure wound therapy system of claim 1, wherein:
    the coating is in the first state when an amount of the fluid in the tube is below a threshold; and
    the coating is in the second state when an amount of the fluid in the tube is at or above the threshold.

7. The negative pressure wound therapy system of claim 1, wherein:
    the flow restriction pad further comprises a connecting layer comprising a hydrophobic portion having hydrophobic properties;
    the flow restriction pad is coupled to the first end of the tube at the hydrophobic portion of the connecting layer; and
    the hydrophobic portion of the connecting layer inhibits the passage of the fluid into the first end of the tube.

* * * * *